(12) United States Patent
Brodland

(10) Patent No.: US 7,762,146 B2
(45) Date of Patent: Jul. 27, 2010

(54) MULTIPLE POINT ATTACHMENT SYSTEM FOR SPECIMEN LOADING OR DEFORMATION

(75) Inventor: G. Wayne Brodland, Waterlo (CA)

(73) Assignee: Waterloo Instruments Inc., Waterloo (CA)

( * ) Notice: Subject to any disclaimer, the term of this patent is extended or adjusted under 35 U.S.C. 154(b) by 0 days.

(21) Appl. No.: 11/672,551

(22) Filed: Feb. 8, 2007

(65) Prior Publication Data
US 2007/0180927 A1 Aug. 9, 2007

Related U.S. Application Data

(60) Provisional application No. 60/771,150, filed on Feb. 8, 2006.

(51) Int. Cl.
G01N 3/02 (2006.01)
G01N 3/08 (2006.01)

(52) U.S. Cl. .............................. 73/856; 73/860; 73/831; 73/826

(58) Field of Classification Search .................. 73/856, 73/857, 798, 794, 831, 819, 813, 818, 159, 73/826; 26/72–73
See application file for complete search history.

(56) References Cited

U.S. PATENT DOCUMENTS

| 2,918,696 | A | * | 12/1959 | Bottoms et al. ................. 38/12 |
| 3,315,301 | A | * | 4/1967 | Dibblee et al. .................. 38/12 |
| 3,807,224 | A | * | 4/1974 | Hassenboehler .............. 73/831 |
| 4,677,854 | A | * | 7/1987 | Gabelli ......................... 73/794 |
| 5,161,674 | A | * | 11/1992 | Rutz et al. ...................... 26/73 |
| 5,468,138 | A | * | 11/1995 | Bosse et al. .................. 425/383 |
| 5,552,006 | A | * | 9/1996 | Soliday et al. .............. 359/847 |
| 5,680,262 | A | * | 10/1997 | Soliday et al. .............. 359/847 |
| 6,168,572 | B1 | | 1/2001 | Vexler et al. |
| 6,247,370 | B1 | * | 6/2001 | Ramaswamy et al. ......... 73/857 |
| 6,289,753 | B1 | | 9/2001 | Basser et al. |
| 6,487,902 | B1 | * | 12/2002 | Ghosh ......................... 73/159 |
| 6,664,067 | B1 | | 12/2003 | Hajduk et al. |
| 6,833,924 | B2 | | 12/2004 | Love et al. |
| 6,860,156 | B1 | * | 3/2005 | Cavallaro et al. ............. 73/819 |

(Continued)

OTHER PUBLICATIONS

Nagatomi et al. "Passive-state viscoelastic properties of normal vs. neurogenic bladder wall tissue" 2003 Summer Bioengineering Conference, Jun. 25-29, pp. 625-626. Accessed online Jun. 7, 2008.*

(Continued)

Primary Examiner—Lisa M Caputo
Assistant Examiner—Jonathan Dunlap
(74) Attorney, Agent, or Firm—Borden Ladner Gervais LLP; Jeffrey W. Wong

(57) ABSTRACT

Stresses or deformations can be applied to a specimen, by at least one carrier having a number of flexible fingers extending therefrom, the fingers being securable to the specimen at spaced-apart locations, the carrier typically being attached to a motion-control and load measuring system. The fingers are relatively rigid in tension (or compression if desired) but flexible with respect to motions in other in-plane directions. They may or may not be flexible in out-of-plane directions. Commonly, there may be two carriers on opposite sides of the specimen for applying substantially uniaxial stress, or four carriers at 90 degrees to each other around the specimen for applying substantially biaxial stress, though any number of carriers may be used.

9 Claims, 14 Drawing Sheets

U.S. PATENT DOCUMENTS 6,936,471 B2  8/2005  Hajduk et al.

OTHER PUBLICATIONS

Waldman et al. "Boundary condtions during biaxial testing of planar connective tissues. Part 1: Dynamic Behaviour" Journal of Materials Science: Materials in Medicine, vol. 13 (2002) pp. 933-938. Acessed online Jun. 7, 2008.*

Instron. "Planar-Biaxial Soft Tissue Test System" Instron Corporation. (2004). Accessed online Jun. 7, 2008.*

Malcolm, D.T.K., et al.; "Strain measurement in biaxially loaded inhomogeneous, anisotropic elastic membranes"; Biomechan. Model. Mechanobiol.; Dec. 2002; pp. 197-210; vol. 1, No. 3; Springer Berlin/Heidelberg.

Green, D.E., et al.; "Experimental investigation of the biaxial behaviour of an aluminum sheet"; International Journal of Plasticity; Aug.-Sep. 2004; pp. 1677-1706; vol. 20, Nos. 8-9; Elsevier Science Ltd.

Sun, W., et al.; "Effects of Boundary Conditions on the Estimation of the Planar Biaxial Mechanical Properties of Soft Tissues"; Journal of Biomechanical Engineering; Aug. 2005; pp. 709-715; vol. 127, No. 4; ASME.

* cited by examiner

MULTIPLE POINT ATTACHMENT SYSTEM FOR SPECIMEN LOADING OR DEFORMATION

BACKGROUND OF THE INVENTION

1. Field of the Invention

This invention relates to multiple point attachment to specimens, for biaxial or uniaxial loading, deformation or testing.

Situations exist where it desirable to induce specified loads, deformations or strain states in materials, specimens or objects or to restrain them against motions that would otherwise occur. These include situations where mechanical properties are determined by applying particular loads or combinations of loads in different directions or loading in one direction with or without restraint in another. Other situations include, but are not limited to, manufacturing processes, preconditioning of materials, use of stress or strain states to induce fiber alignment, crystallization in the material or situations where it is desired to otherwise regulate, alter or transform the material's properties or structure at the bulk, meso, micro or nano scale.

Attachment to the specimen is often of concern and, to produce specified internal strain or stress fields, careful design of the specimen and its loading system may be required, especially if uniform or other specified fields are desired or if large deformations are involved.

2. Description of the Prior Art

There are several methods known in the art used to load materials. One of the key difficulties is attachment of the load system to the specimen.

The three primary methods can be characterized as either structured specimen methods, substrate methods or attachment methods.

Structured Specimen Methods

Structured specimen methods are characterized as structuring the material into a geometry that facilitates loading and deformation control. A well-known version of this is the pressurized cylinder test, in which the material of interest either occurs as a cylindrical shape or is formed into one. The ends of the specimen are clamped to circular end plates. By controlling the pressure inside the hollow specimen and controlling the spacing between the end plates, through load or deformation, the stresses and strains in the hoop and axial directions can be controlled independently. Primary loading is in the local tangent plane to the specimen; i.e., the loading is "in-plane".

This method has the advantage of allowing the in-plane conditions to be specified independently (subject to certain limitations). It works well for testing of tubes or blood vessels.

Substrate Methods

Substrate methods are characterized as affixing the material to be tested onto a substrate material. The substrate is then loaded by stretching it in a known manner, thus also stretching the material under test.

For example, Love et al. (U.S. Pat. No. 6,833,924 and others) teaches a method where the substrate is secured along its edges and is pressurized to form a dome having a height axis substantially perpendicular to its original plane.

In general with dome substrate methods, the induced stress or strain states are not uniform over the surface of the dome. This method has the advantage that it can perform multi-axial loading since the material is stretched biaxially. Subtracting the effects of the substrate is a source of error in the system.

Attachment Methods

The third method can be characterized as attachment methods. The invention is related to this classification of test method. The attachment method is generally characterized as taking a small section of the material (a specimen) to be tested and attaching to it in such a manner that the edge load or deformation can be specified in one or more axes. Attachment of the load to the material is known to be problematic in the art. Gripping, clamping, hooks and suture attachments are known. Substantially different experimental results can be obtained using different gripping methods on the very same specimen. Sun et al. (Journal of Biomechanical Engineering, August 2005, Vol. 127/709) teaches the importance of attachment geometry in planar biaxial testing. They conclude that suture based methods are a preferred attachment method for biaxial mechanical testing of biological materials.

Gripping or Clamping Methods.

One approach is to cut the specimen into a square and clamp along each edge as shown in FIG. 1a.

Another approach is cut the specimen into an "X" or "t" shape (also known as a cruciform method) and clamp on the arms as shown in FIG. 1b.

Attachment Point Methods

Still another approach is to have a number of attachment points along the edges of the specimen. For biaxial or uniaxial testing the attachments must be stiff in the direction in which they are pulling or pushing and flexible in the other in-plane direction. Sutures are attached through the specimen along the edge of the specimen, and such sutures are considered state of the art. They simultaneously satisfy the stiffness and flexibility requirements. Sutures are shown in FIG. 1c. Hooks attached to sutures have also been used as shown in FIG. 1d. This method reduces the artificial stiffening at the boundaries.

SUMMARY OF THE INVENTION

It is an object of the invention to provide an improved specimen attachment system for biaxial or uniaxial testing.

In the invention, a series of "fingers" are attached to a carrier, which is typically attached to a motion-control and load measuring system. The fingers are attached to the specimen at specific attachment sites. The fingers are relatively rigid in tension (or compression) but flexible with respect to motions in other in-plane directions. They may or may not be flexible in out-of-plane directions.

The invention provides an integrated specimen attachment system that can be engineered for specific loading conditions. It can be designed to have a different and controllable tension or compression in-axis, off-axis and out-of-plane. The attachment, connection and carrier elements are integrated into a single system facilitating handling and attachment and improving repeatability. A number of fingers can be used with consistent alignment to avoid unintentional variability.

Other features of the invention will be described or will become apparent in the following description of preferred and exemplary embodiments, taken together with the accompanying drawings.

BRIEF DESCRIPTION OF THE DRAWINGS

The invention will now be described in detail, with reference to the accompanying drawings of preferred and exemplary embodiments, in which:

FIG. 3b is a block diagram of a more complex variation of the FIG. 2a embodiment, in which there are four of the fundamental building blocks shown in FIG. 2a;

DESCRIPTION OF THE PREFERRED EMBODIMENTS

Figure 1A:
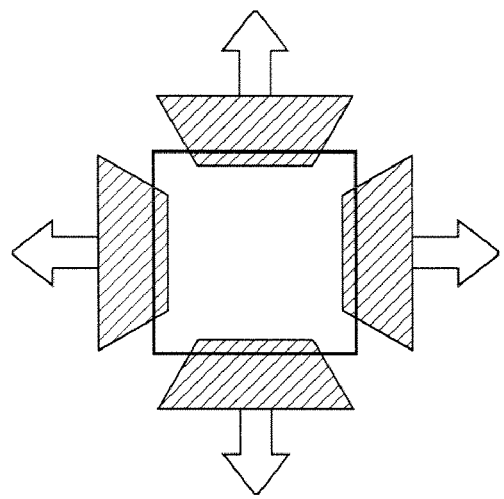
FIG. 1a (prior art) is a schematic illustration of a prior art clamping method.
Figure 1B:
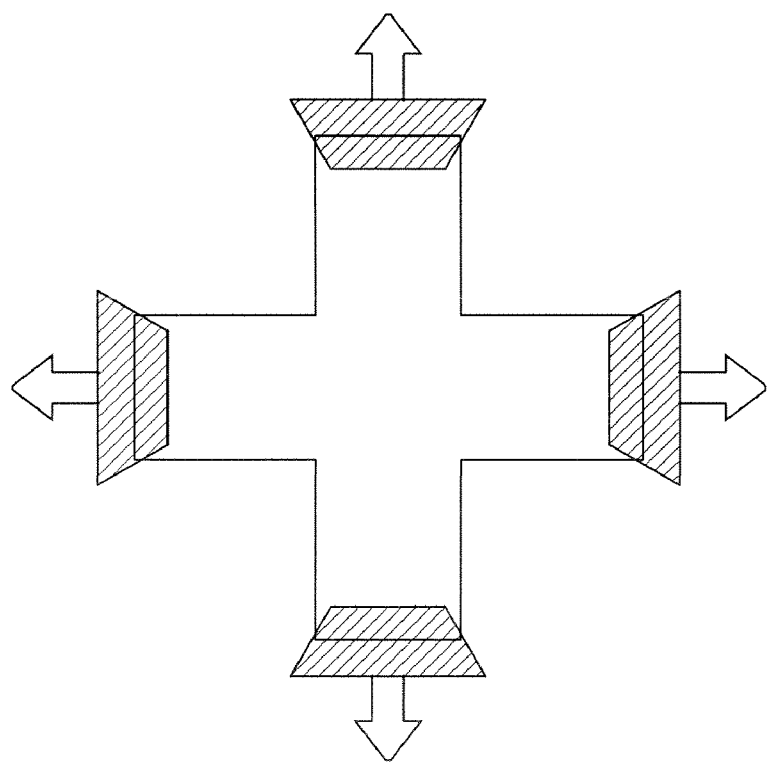
FIG. 1b (prior art) is a schematic illustration of a prior art cruciform method.
Figure 1C:
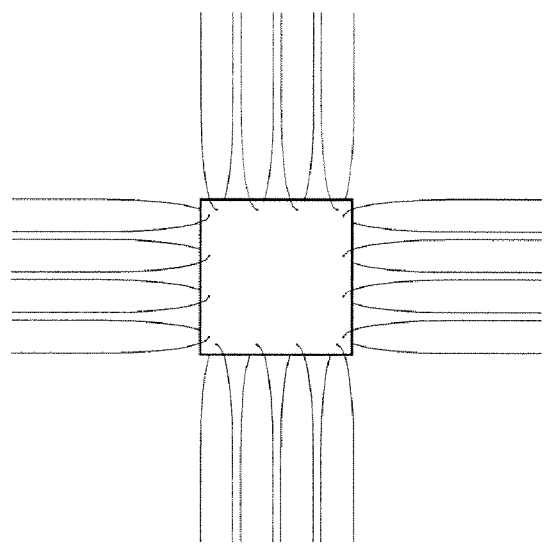
FIG. 1c (prior art) is a schematic illustration of a prior art suture method.
Figure 1D:
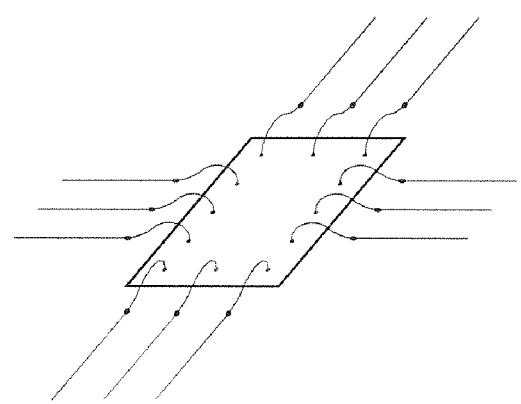
FIG. 1d (prior art) is a schematic illustration of a prior art hook method.
Figure 2:
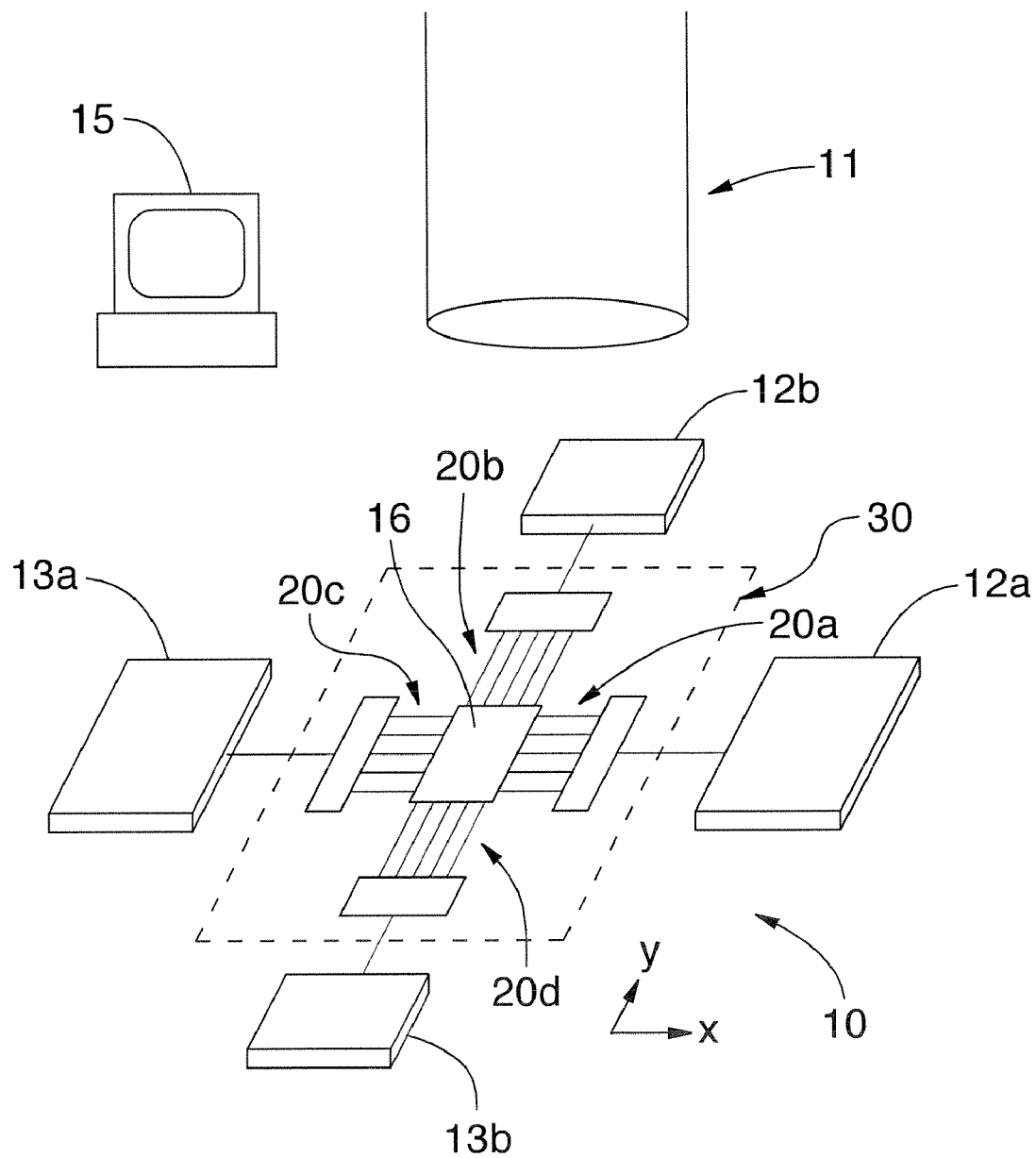
FIG. 2 is a schematic illustration of a complete multiple attachment point system for biaxial load mechanical testing, the invention being a part of this whole system.

FIG. 2 shows a complete biaxial load measurement system 10 schematically. A vision system 11 is used to measure the displacement of fiducial markers (not shown in FIG. 2) on the specimen 16 during its initial state and during loading. Fiducial markers may be artificially placed on the test specimen 16 or they may be naturally occurring. A specimen can be almost anything but for this example only, consider the specimen to be a small amount of tissue from a human heart valve 4 mm square. Component 12a provides computer controlled linear motion causing stress [motion] in the X-axis and 12b provides similar stress [motion] in the Y-axis. Components 13a and 13b measure the load in the X and Y directions respectively. The measured stress is readable by the computer 15. The vision system 11, fiducial tracking methods, the loading system 12a and 12b and the load measurement system 13a and 13b are well known in the art and are not part of the invention. They are shown for clarification and understanding of the application and to increase the understanding of the problems that the invention are solving. The invention resides in the multiple attachment point system for uniaxial loading, further referred to herein as the "uniaxial mount" for simplicity. In this exemplary embodiment, there are four uniaxial mounts 20a, 20b, 20c and 20d according to the invention, forming the system defined by area 30 in FIG. 2. The uniaxial mount 20a is physically anchored to the X linear motion control 12a and the uniaxial mount 20c is physically anchored to the stationary X load measurement system 13a. The uniaxial mounts 20b and 20d are likewise attached to the Y axis linear motion control 12b and Y load measurement system 13b respectively. The sections of the individual uniaxial mounts and the combined biaxial mount system in area 30 will be described in more detail below.

In a typical test, the specimen 16 is attached to uniaxial mounts 20a, 20b, 20c and 20d, as described in detail below. The resulting biaxial mount system 30 is placed in the test system 10. A computer 15 will control the amount of load placed in the X and Y-axes (by components 12a and 12b respectively) while measuring the displacement of the fiducials of the specimen 16 with the vision system 11, while at the same time measuring the stresses in the X and Y axes (by components 13a and 13b respectively). These measurements taken together allow the system to determine mechanical properties of the specimen 16.

Figure 3A:
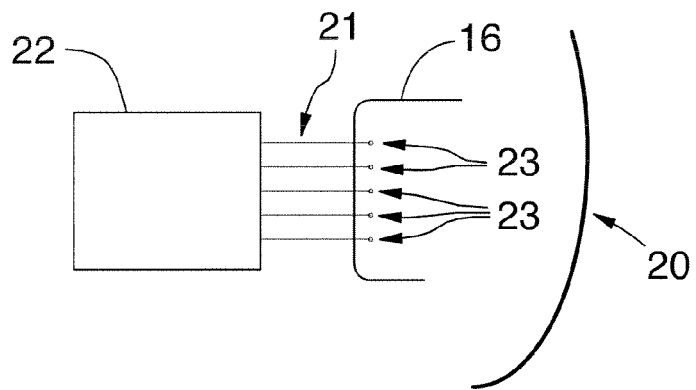
FIG. 3a is a schematic illustration of a very simple embodiment of the invention, namely a multiple attachment point system for uniaxial or biaxial loading, hereinafter referred to as a uniaxial mount for simplicity.

FIG. 3a shows a uniaxial mount 20 in more detail. A series of "fingers" 21 are attached to a carrier 22. The fingers 21 are attached to the specimen 16 at specific attachment sites 23.

Figure 3B:
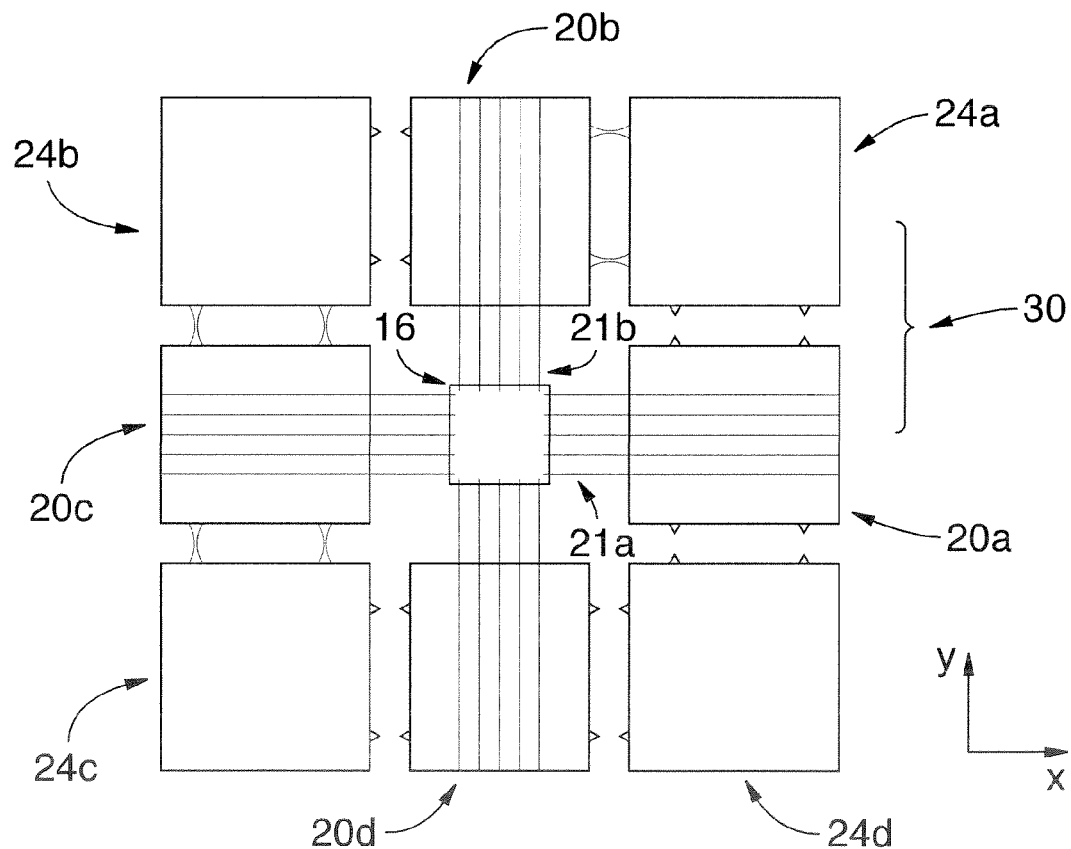

FIG. 3b shows a typical biaxial mount system 30 according to the invention in more detail. There are four uniaxial mounts 20a, 20b, 20c and 20d placed at 90 degree increments around the specimen 16. Tabs 24a, 24b, 24c and 24d are located between the uniaxial mounts and act as an extension of the carrier 22. These tabs are optional and can be used to simplify manufacturing or may be used to increase mounting options. The tabs have been shown in system 30 as being break-away in nature, but other attachment methods are possible, as known in the art. The uniaxial mounts 20a and 20c are free to move in the X direction and are attached to the loading subsystem 12a and 13a. The uniaxial mounts 20b and 20d are free to move in the Y direction and are attached to the loading subsystem 12b and 13b respectively.

Referring again to FIG. 2 and FIG. 3b, stress is applied in the X direction by the X load 12a when signaled by computer 15. The fingers 21a are parallel to the X-axis and transfer the stress to the specimen 16 in the X direction. The X fingers 21a are rigid in the X direction and flexible in the Y direction. The fingers may or may not be flexible out-of-plane in the Z direction. The Y fingers 21b are parallel to the Y axis and they will bend freely in the X direction as stress is placed on X fingers 21a.

Similarly, stress is applied in the Y direction by the Y load 12b when signaled by computer 15. The fingers 21b are parallel to the Y-axis and transfer the stress to the specimen 16 in the Y direction. The Y fingers 21b are rigid in the Y direction and flexible in the X direction. The fingers may or may not be flexible out-of-plane in the Z direction. The X fingers 21a are parallel to the X-axis and they will bend freely in the Y direction as stress is placed on Y fingers 21b.

Figure 4A:
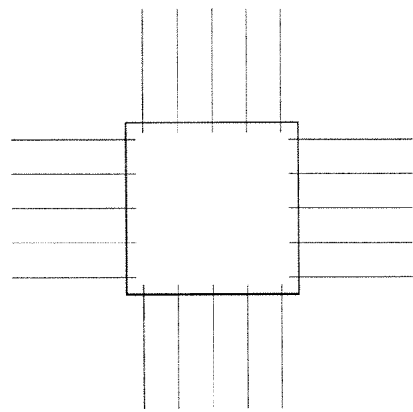
FIG. 4a shows the invention under initial conditions.
Figure 4B:
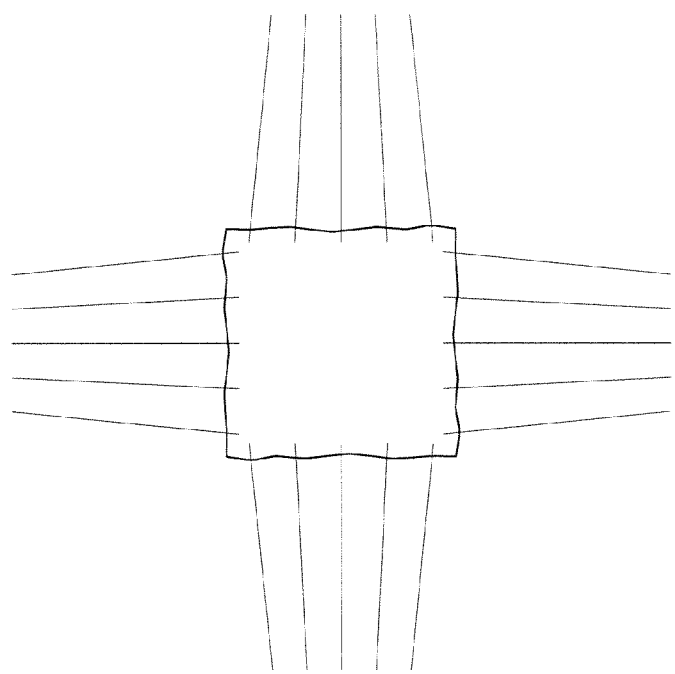
FIG. 4b shows the invention under deformed conditions.

When no load is present in the X and Y directions, the specimen 16 is undisturbed, as shown in FIG. 4a. When stress is applied in both the X and Y directions simultaneously, then the specimen 16 is deformed, as shown in FIG. 4b.

Figure 4C:
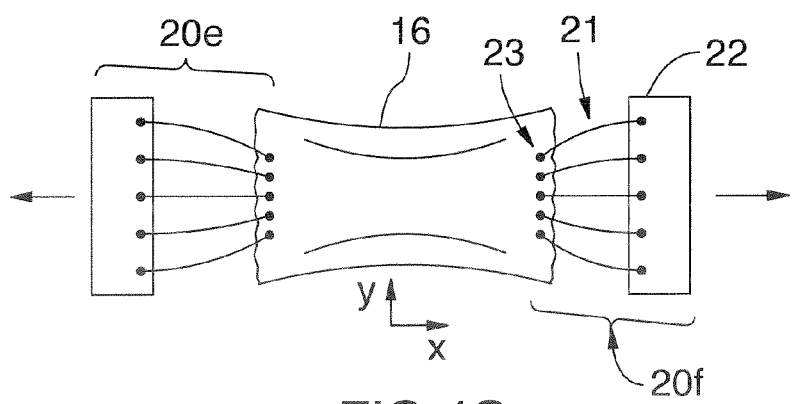
FIG. 4c shows the invention in a uniaxial configuration under deformed conditions.

FIG. 4c shows a uniaxial configuration in which stress is applied in the X direction only, using two uniaxial mounts 20e, 20. Note the deformation of the fingers 21 in the Y direction that occurs due the material properties of the test specimen. The uniaxial mount 20 device has been optimized for biaxial testing but FIG. 4c shows that it is also very suitable as an improved multiple point attachment system for uniaxial testing.

Fingers 21 can be designed to have different tension or compression in the primary axis direction, off-axis direction and out-of-plane directions, as needed by the application. Specifically for X fingers 21a the primary axis direction is X, the off-axis direction is Y and the out-of-plane direction is Z. Similarly, for Y fingers 21b the primary axis direction is Y, the off-axis direction is X and the out-of-plane direction is Z.

Figure 5:
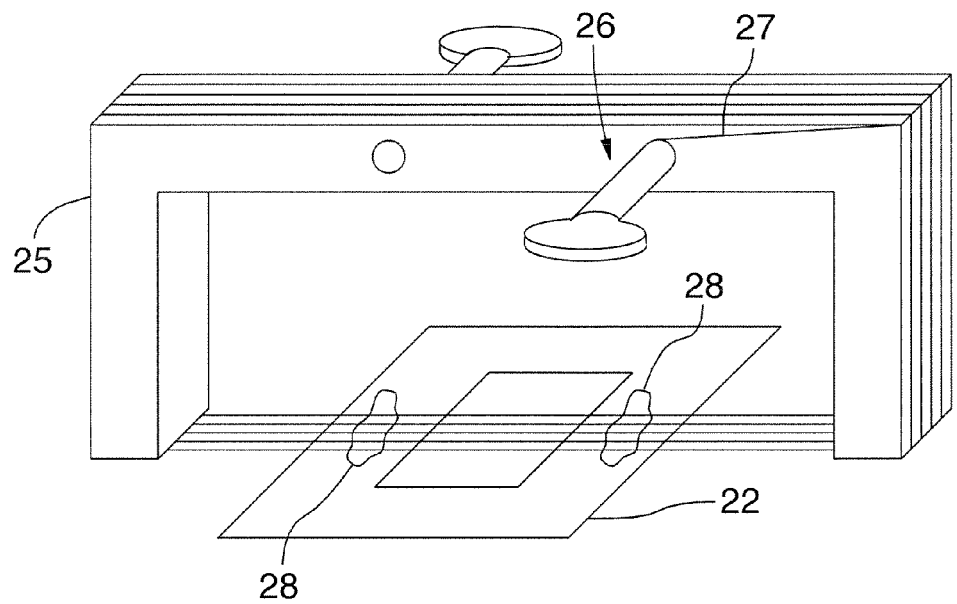
FIG. 5 is a perspective view showing the creation and alignment of wire fingers and the attachment of the wire fingers to the carrier.
Figure 6:
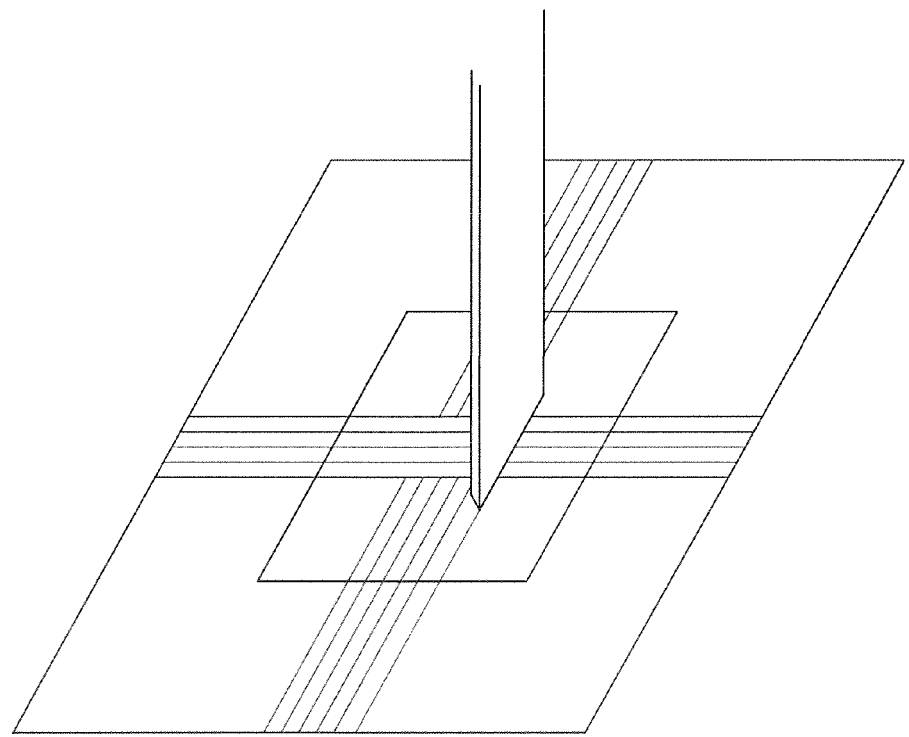
FIG. 6 a perspective view showing the termination creation of the wire fingers to form a simple cut end.

FIGS. 5, 6, 7a and 7b illustrate the construction of one specific embodiment of the uniaxial mount 20. In this embodiment, the fingers 21 are made from stainless steel wire 27, 0.004 inches in diameter, and the carrier 22 is made from acrylic. The wire is wound on an alignment frame 25 as shown in FIG. 5. Tension is applied by turning the key 26 to ensure the wires 27 are parallel and placed as required in a repeatable and controlled manner. The wires 27 are placed touching the surface of the carrier 22. A fixture can be used to ensure repeatable placement of the wire relative to the carrier 22. The wires are glued to the carrier with cyanacrylate 28. FIG. 6 shows the wire being cut with a sharp chisel-like punch, forming a simple cut end. This entire process is repeated for the perpendicular direction and then the uniaxial mount 20 is complete.

Figure 7A:
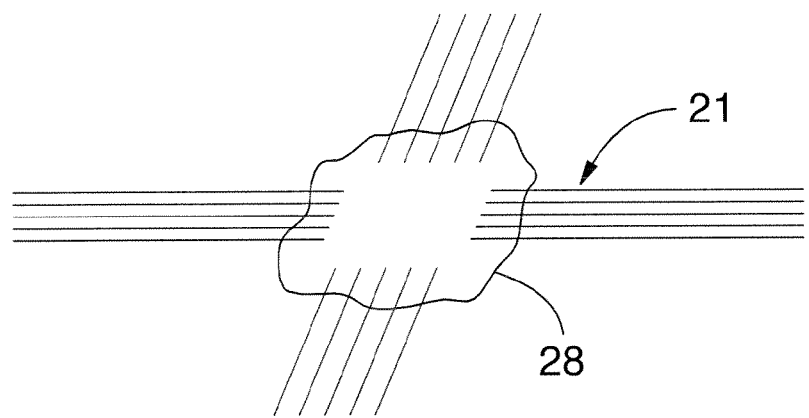
FIG. 7a shows the fingers being dipped in glue.
Figure 7B:
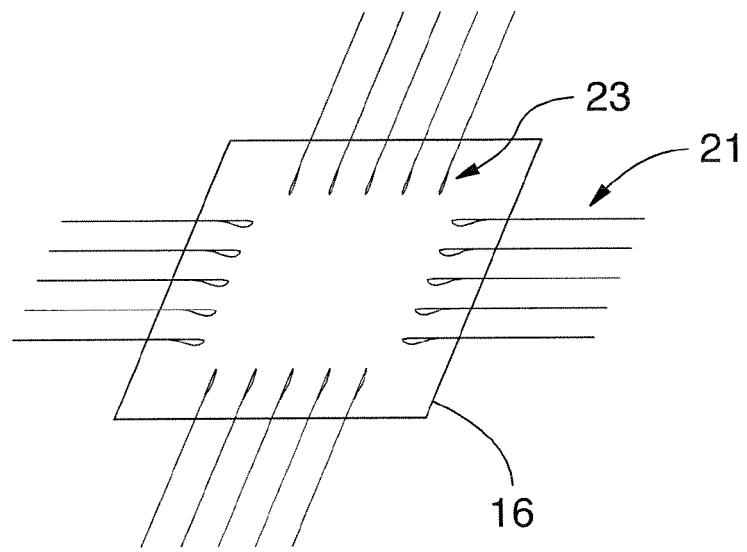
FIG. 7b shows the attachment of the fingers to a specimen.

FIGS. 7a and 7b show a variation of the method of attaching specimen 16 to the uniaxial mount 20. In this variation, the fingers 21 are first placed onto the glue cyanacrylate 28 (FIG. 7a). Then the fingers are placed onto specimen 16 at the specific attachment sites 23 (FIG. 7b). The fingers 21 are still covered with glue, which will bond to the specimen 16.

FIGS. 8a-8g show variations of the design of the fingers 21. In general, parameters of the finger tension properties in-axis, off-axis and out-of-plane can be engineered by changing the geometry and/or the materials. Tension variance along the length of the finger 21 can be obtained by varying the cross sectional geometry and/or varying the material composition along the length. A composite material can be used. Other methods of construction are listed below.

Figure 8A:
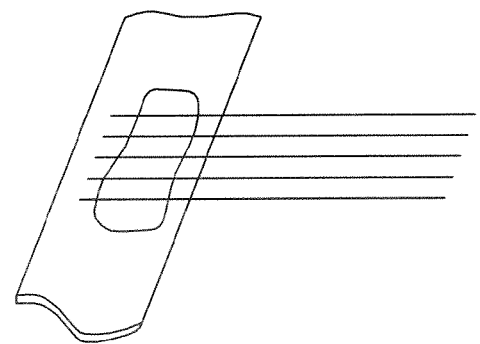
FIG. 8a shows an example of the finger design being wire.

FIG. 8a shows the use of wire, as in the above description. Wire is relatively easy to work with but does not have the advantage of configurable anisotropic behavior off-axis and out-of-plane.

Figure 8B:
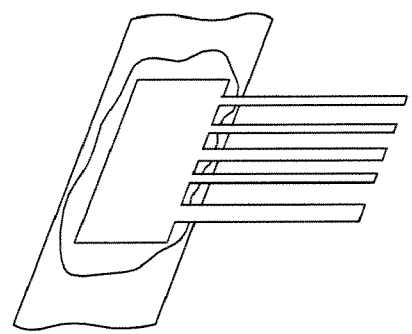
FIG. 8b shows an example of the finger design being foil.

FIG. 8b shows the use of foil, which has nearly ideal properties for many applications of this invention. It can be mass manufactured with various precise methods described below. By changing the dimensions of the material in width and thickness different tension can be obtained off-axis and out-of-plane as desired.

Figure 8C:
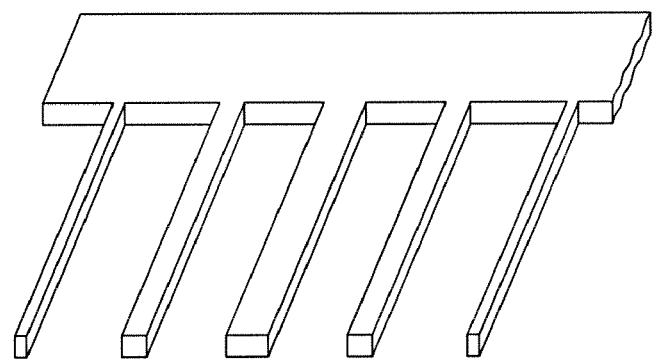
FIG. 8c shows an example of the finger design having geometric variations from finger to finger to change stiffness.

FIG. 8c shows the use of geometric variations. These geometric variations from finger to finger can change stiffness across the specimen as desired.

Figure 8D:
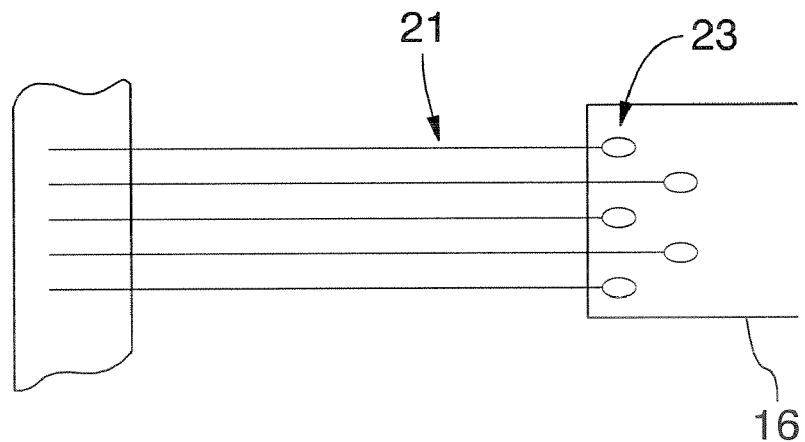
FIG. 8d shows a pattern to allow close packing.

FIG. 8d shows the use of a pattern which allows close packing of attachment points 23 to the specimen 16.

Figure 8E:
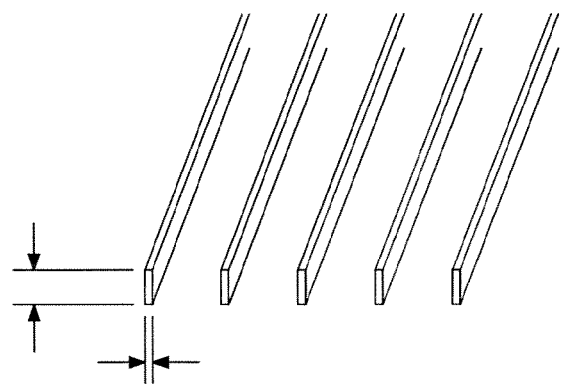
FIG. 8e shows and example of rigid out-of-plane fingers to facilitate attachment or loading or to provide through-thickness attachment.

FIG. 8e shows the use of a rigid out-of-plane foil material, having a very thick finger relative to the width, causing the out-of-plane stress to be very rigid.

Figure 8F:
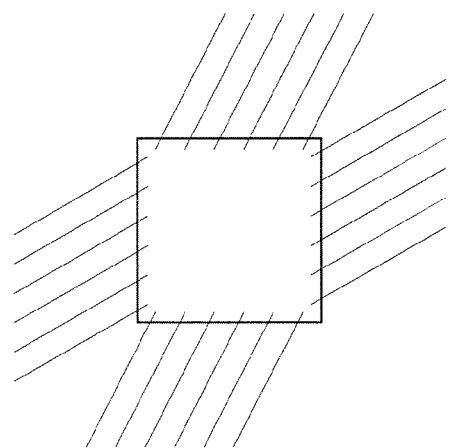
FIG. 8f shows angled fingers to facilitate loading having a shear component or deformation that produces same.

FIG. 8f shows a finger arrangement which is angled to facilitate loading having a shear component or deformation that produces same.

Figure 8G:
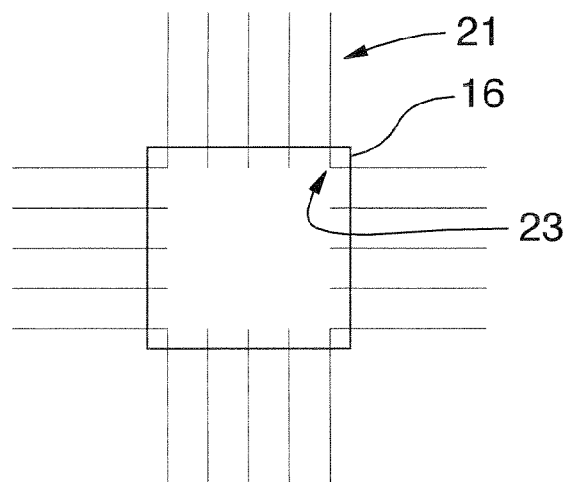
FIG. 8g shows bi-directional corners.

FIG. 8g shows the use of bi-directional corners which can be easily produced, where the corner fingers are attached to the same attachment site 23 of the specimen 16. This facilitates alignment of four elements.

In addition, composite materials can be produced that have different properties in different axes. The composition can be also varied along the length of the finger 21.

Figure 9A:
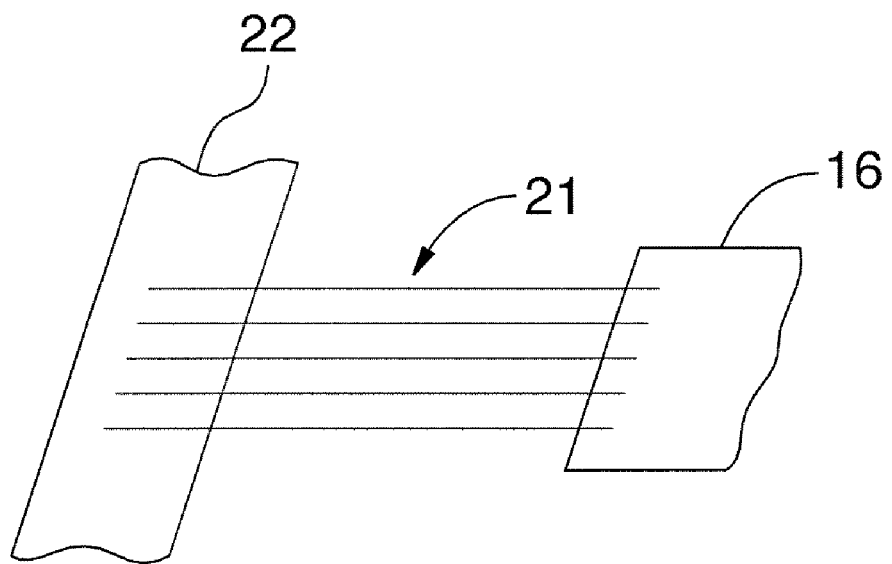
FIG. 9a shows a variation where there is air between fingers (i.e. fingers fixed at carrier only)
Figure 9B:
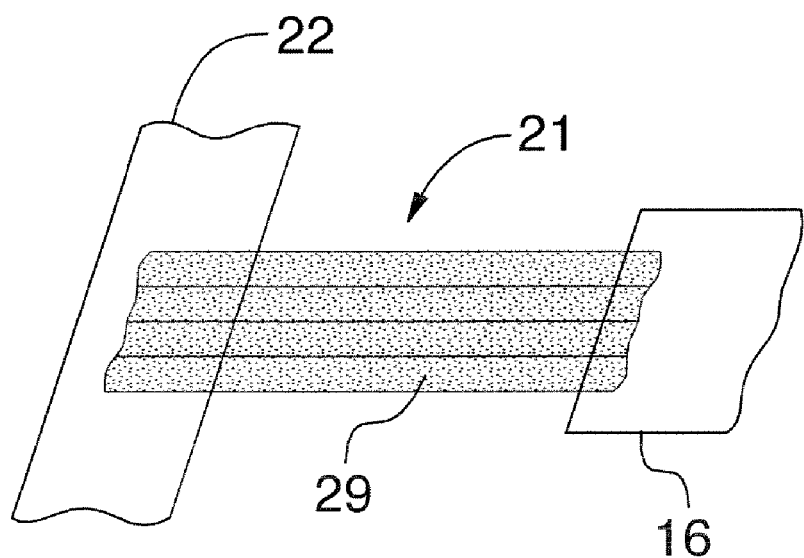
FIG. 9b shows a variation where there is webbing (i.e. fingers having a secondary carrier between the primary carrier and the attachment to the specimen)

FIGS. 9a and 9b show variations of the space between fingers 21. In FIG. 9a there is no material between the fingers 21 in the space between the frame of the carrier 22 and the specimen 16. In FIG. 9b the fingers have a secondary carrier (webbing) 29 between the primary carrier 22 and attachment to specimen 16. This webbing can be engineered to change the stress properties of the fingers off-axis as desired.

An engineered material with anisotropic mechanical properties can be used to fabricate a unified finger.

FIGS. 10a-10d show variations of the termination of fingers 21.

Figure 10A:
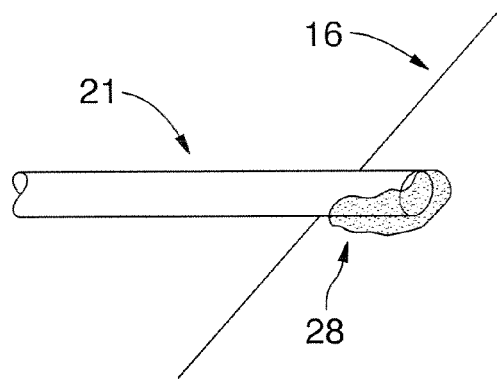
FIG. 10a shows an example of a simple finger termination, with attachment to the top surface of the specimen.

FIG. 10a shows a simple termination, where the finger 21 terminates abruptly with a simple cut. Attachment of this type of finger is made to the top surface of the specimen 16 with glue 28, for example.

Figure 10B:
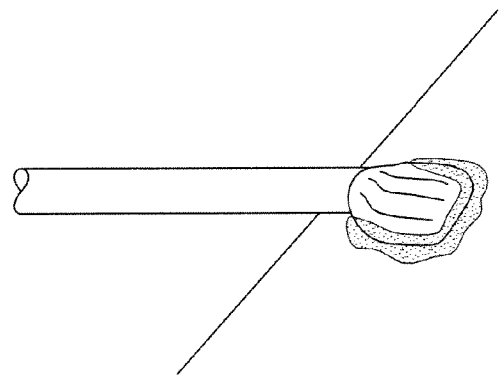
FIG. 10b shows a pad attachment to the top surface of the specimen.

FIG. 10b shows a pad, with the finger being deformed at the termination end to form a larger surface area for attachment to the top surface of the specimen 16 with glue 28.

Figure 10C:
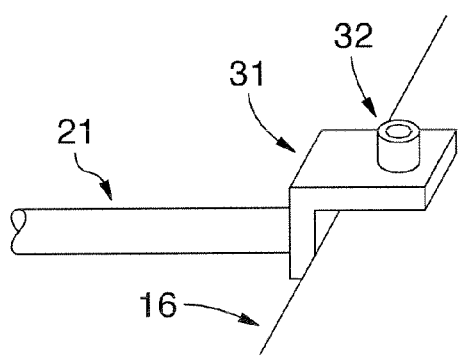
FIG. 10c shows a hook or pin attachment by penetration through the specimen.

Hook or pin: FIG. 10c shows a sharp mechanical structure 32, i.e. a hook or pin, inserted through the specimen 16 and through two sides of the fork 31. This is designed for attachment by penetration through the specimen 16.

Figure 10D:
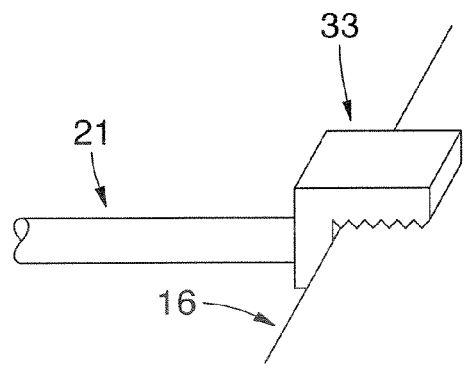
FIG. 10d shows a micro-grip attachment by gripping or friction with the top and bottom surfaces of the specimen.

FIG. 10d shows a micro-grip, i.e. a set of jaws 33 designed for attachment by gripping the top and bottom surfaces of the specimen 16.

Figure 11:
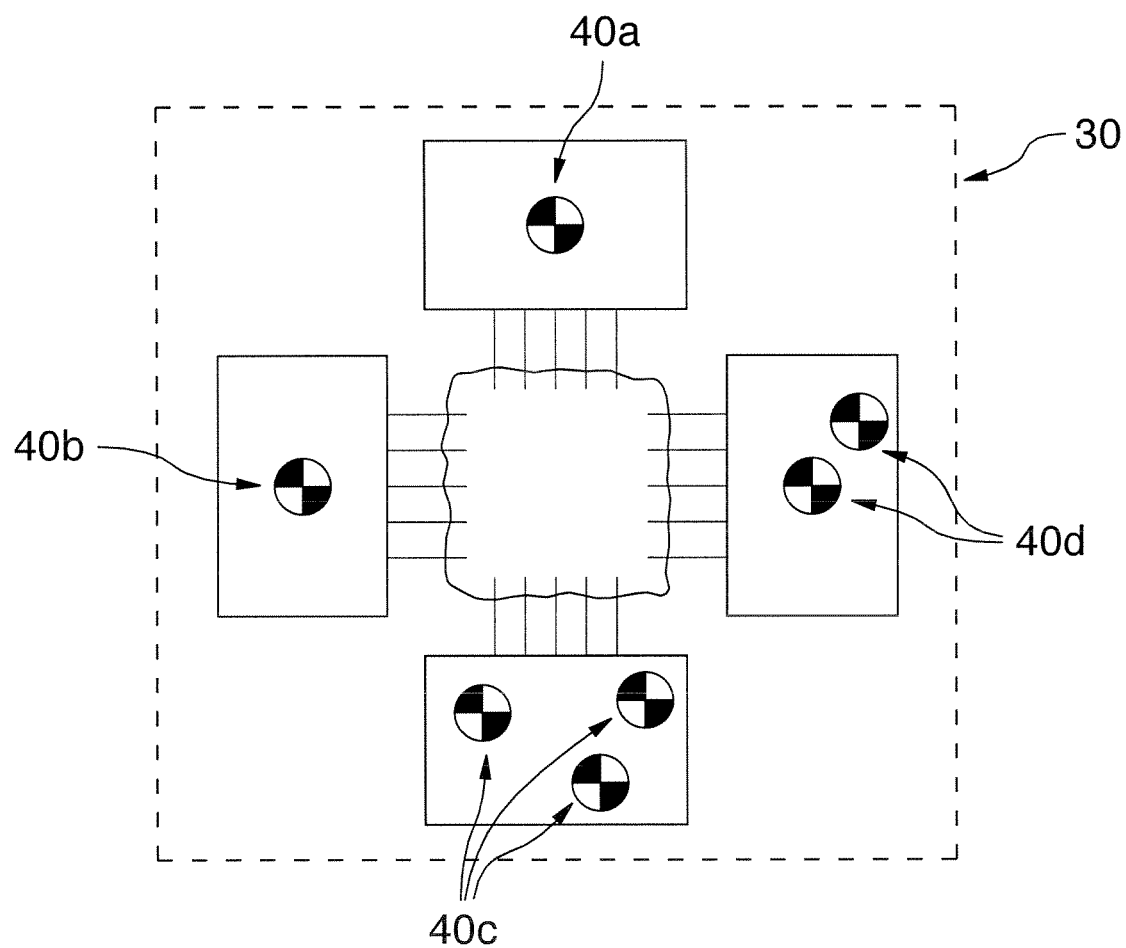
FIG. 11 is a schematic illustration of a biaxial system with fiducial markers located on the finger carriers.

FIG. 11 shows a method of measuring the finger carrier 22 position. Fiducial markers 40a-40d are placed on the finger carrier 22. These markers are visible to a machine vision system 11 (see FIG. 2). The markers may be simple dots, rings or patterns that are more complex. Generic Target patterns are shown in FIG. 11.

A single target such as 40a and 40b would allow the displacement of the carrier 22 to be measured. Two degrees of freedom can be measured from a single target constrained to planar motion. Typically, the motion is further constrained to a single axis. Fiducial targets 40d show two targets and 40c shows the use of three targets. The plurality of targets are used for determining higher degrees of freedom for the position and orientation of the carrier 22, if such information is of interest, and if the carrier has freedom of movement. As is well known in the art, 5 degrees of freedom can be determined from the 3D position of 2 targets, and 6 degrees of freedom can be determined from the 3D position of 3 targets. The relative location of the targets is known.

Figure 12:
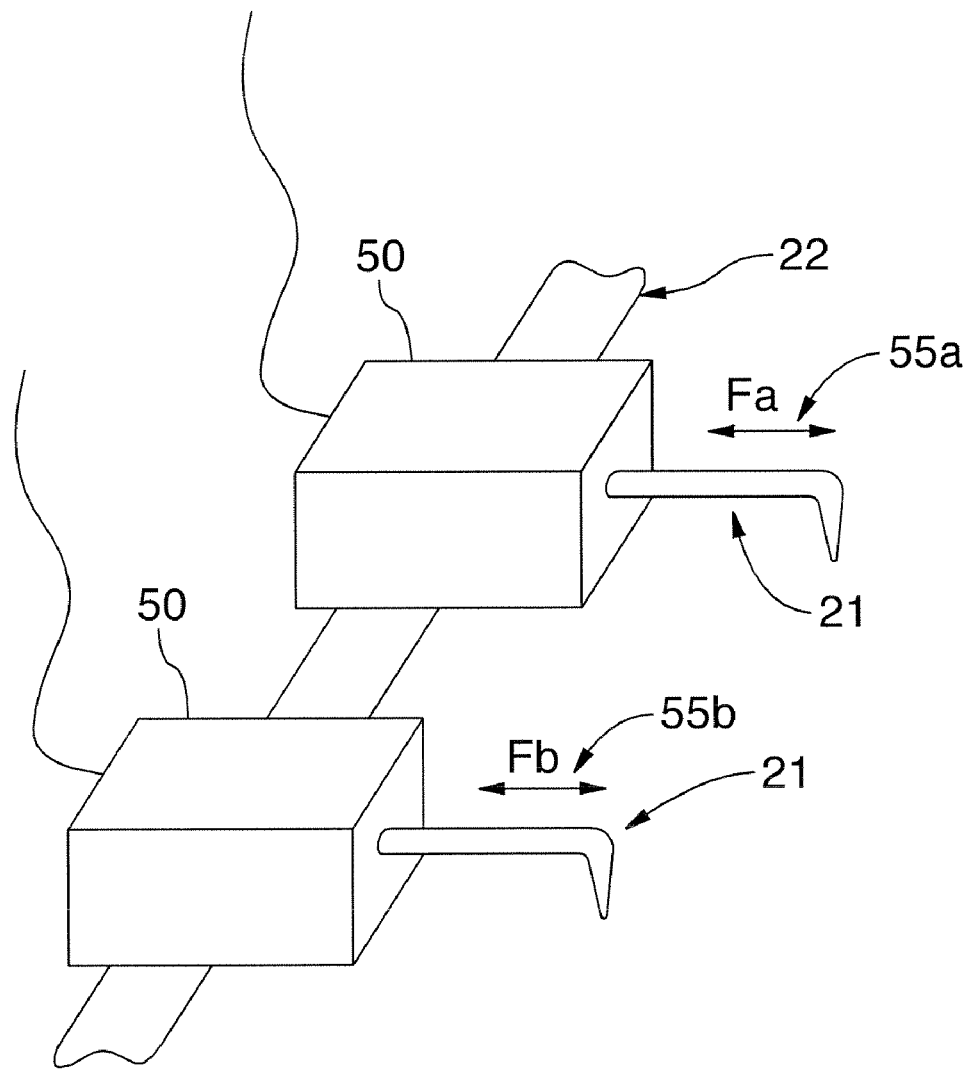
FIG. 12 is a schematic illustration of a subsystem located on each individual finger that provides individual force application, and finger linear displacement measurement.
Figure 13A:
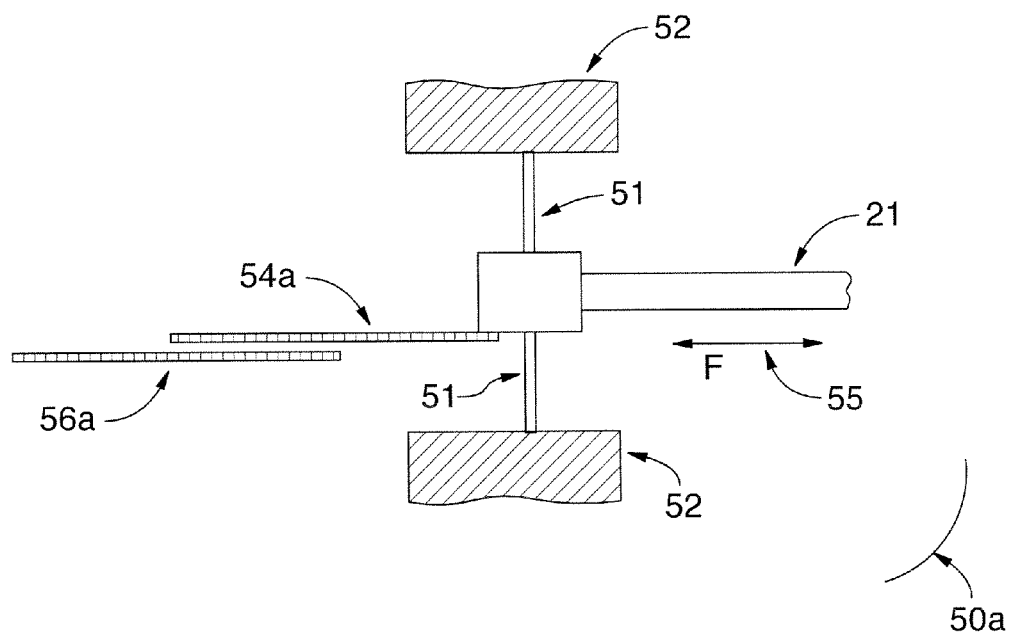
FIG. 13a is a schematic illustration of a stress and displacement subsystem with individual sections that produce load and measure linear displacement.
Figure 13B:
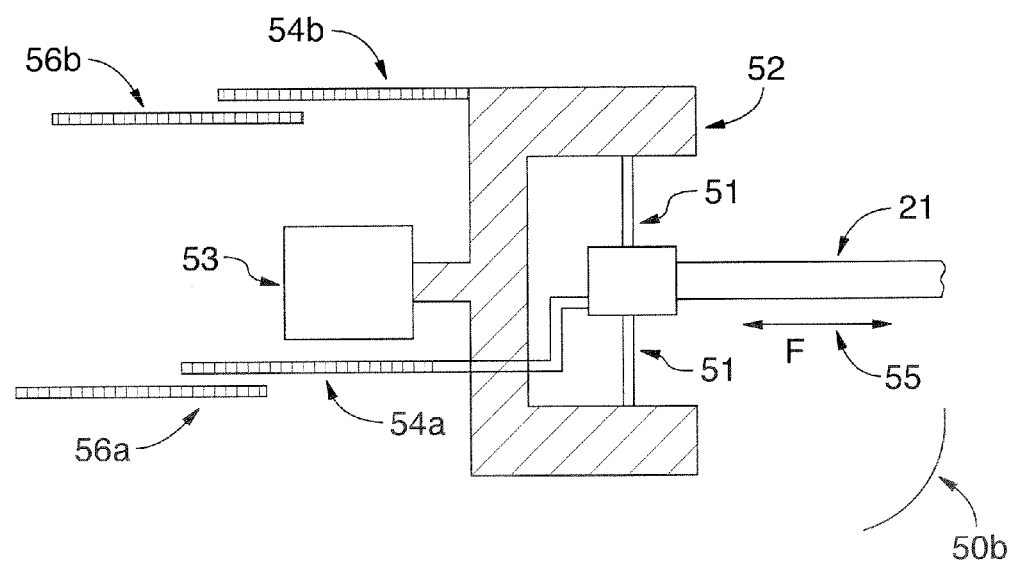
FIG. 13b is a schematic illustration of a further stress and displacement subsystem with individual sections that produce load and measure linear displacement.

Referring now to FIGS. 12, 13a and 13b, a load displacement subsystem 50 will be described. This subsystem is used on individual fingers 21 in conjunction with the full system 10 (FIG. 2). It is not a requirement that each finger 21 be instrumented with subsystem 50. FIGS. 13a and 13b are two variants of the manner of implementation.

The following is common to both variants. The finger 21 is held in place by a plurality of beams or struts 51 of which two are shown in FIGS. 13a and 13b. The finger 21 is considered at position zero when the beams are in their minimum stress state. The beams are anchored to a frame 52. The end of the finger 21 connected to the beams is constrained in motion to a single axis along the length of the finger 21. The force 55 applied along finger 21 will cause the beams 51 to deflect.

The displacement of the finger 21 can be determined by the use of a plurality of capacitor plates 54a, 56a or other position sensor of which two are shown in FIG. 13a. and FIG. 13b. Plate 54a is attached to the finger and is free to move along one axis. Plate 56a is a stationary plate anchored to frame 52. The capacitance varies linearly and directly proportional to the displacement of the finger 21. As is known in the art the capacitance can be measured and the displacement is therefore determined from the capacitance. Likewise, the position of the anchor frame 52 can optionally be determined by using capacitor plates 54b and 56b as shown in FIG. 13b.

Methods other than variable capacitance are also known in the art for displacement measurement, including for example variable resistive measurements, optical targets, triangulation, etc.

The subsystem 50 has at least two variations of operation. In the first variant as shown in FIG. 13a, the beams 51 have a non-negligible stiffness and the anchor frame 52 is stationary. The force 55 upon the finger 21 is determined by measuring the displacement of the beams 51 using the variable capacitor 54a, 56a and knowing the mechanical properties of the beams 51. This method of using beam 51 displacement equations for force measurement allows for the determination of extremely small forces that cannot be measured with state of the art force transducers. In this mode all subsystems 50a connected to the carrier 22 in FIG. 12 are displaced in the same amount. It is then possible to measure the individual forces on each finger 21 that has been instrumented with subsystem 50a.

In the second variant as shown in FIG. 13b, the beams 51 have a non-negligible stiffness and the anchor frame 52 is attached to a linear actuator 53. The actuator 53 is stationary and can displace the anchor frame 52. The force 55 upon the finger 21 is determined by measuring the displacement of the beams 51 using the variable capacitor 54a, 56a and knowing the mechanical properties of the beams 51. In this variant all subsystems 50b can be displaced at an individual amount, thus allowing each finger 21 to have an individually applied load. It is then possible to both measure and control the individual forces on each finger 21 that has been instrumented with subsystem 50b. This variation allows for interesting use of feedback from either the optional anchor displacement measurement capacitors 54b and 56b and the beam measurement capacitors 54a and 54b. If the linear actuator 53 displacement is not sufficiently accurate, the anchor displacement measurement capacitor 54b and 56b can be used in closed loop. Insufficient open loop accuracy is very likely when using a miniature actuator that may have displacements dependant on the load seen by the actuator as well as the actuator control signal.

The force measurement provided by beam displacement measurement capacitor 54a and 56a can be used in a closed loop path controlling the displacement of linear actuator 53 such that a specified force 55 can be arbitrarily and accurately applied to finger 21.

Subsystem 50 may be implemented using micro electronic machining (MEMs) technology. The linear actuator 52 can be implemented with a MEMs electrostatic device.

The uniaxial mount 20 can be secured to the specimen 16 by any suitable means, including the following:
    a. Adhesion methods
    b. Glue (eg., cyanacrylate)
    c. Biological (eg., fibronectin)
    d. Mechanical (eg., hook)
    e. Surface treatment surface texture
    f. Bioactive surface (eg., bioglass)
    g. Freezing (e.g., as by pre-cooling of the fingers)
    h. Heating (e.g., as by cauterizing)

The uniaxial mount 20 can be fabricated by any suitable method, including the following:
    a. Micromachining (e.g., laser cutting)
    b. Microinjection molding
    c. Micro-assembly
    d. Stamping
    e. Microcircuit fabrication methods
    f. Etching
    g. Deposition The uniaxial mount 20 can be made from any suitable material, including the following:
    a. Metal
    b. Glass
    c. Polymer
    d. Elastomer
    e. Ceramic
    f. Composite
    g. Microcircuit material Although only the wire finger embodiment is thoroughly described above, other variations as itemized above will be readily appreciated by those knowledgeable in the field of the invention.

It should also be readily understood that although most references above are to two or four carriers, any number of carriers could be used, and they could be offset from each other by any desired angle or angles, to apply stresses or deformation to a specimen in any desired directions. For example, there could be three carriers, likely but not necessarily offset from each other by 120 degrees. Or there could be 5, 6 or more carriers, in order to produce a corresponding number of different loading points on the specimen.

Similarly, it should be understood that although the vast majority of applications for the invention will have the fingers in tension, the invention may be readily adapted to apply compressive forces. Obviously, in such cases the fingers would have to have sufficient rigidity to prevent buckling thereof.

The invention claimed is:

1. Apparatus for applying loads or inducing strains to a medical specimen, comprising at least one carrier having a plurality of extensions therefrom, the extensions being securable to the medical specimen at spaced-apart locations, whereby stresses or strains can be applied to said medical specimen via said carrier; and wherein the extensions have engineered lateral stiffness and flexibility wherein at least one of the plurality of extensions has a length, in a first direction not parallel to a load path of the carrier, which is longer than a length of the extension in a second direction, the second direction being perpendicular to the first direction and also perpendicular to the load path direction of the carrier;

wherein the engineered lateral stiffness allows for controlled securing of the extension to the medical specimen and the engineered flexibility allows the extensions to flex after being secured to the medical specimen and to have a negligible effect on loading.

2. The apparatus of claim 1, comprising at least two said carriers on opposite sides of said medical specimen, whereby applying loads or inducing strains to said at least two carriers induces substantially uniaxial stress in said medical specimen.

3. The apparatus of claim 1, comprising at least four said carriers spaced apart from each other around said medical specimen.

4. The apparatus of claim 3, comprising four said carriers spaced substantially at 90 degrees to each other around said medical specimen, whereby applying loads or inducing strains to said four carriers induces substantially biaxial stress in said medical specimen.

5. The apparatus of claim 1, comprising three said carriers spaced substantially at 120 degrees to each other around said medical specimen.

6. The apparatus of claim 1 wherein the extensions are securable to said medical specimen via an adhesive.

7. The apparatus of claim 6 wherein the adhesive is glue.

8. The apparatus of claim 1 wherein the extensions are securable to said medical specimen via a hook, without a suture.

9. The apparatus of claim 1 wherein the extensions are securable to said medical specimen via a micro-grip.

* * * * *